United States Patent [19]

Fischer

[11] Patent Number: 4,946,461
[45] Date of Patent: Aug. 7, 1990

[54] TOOL FOR REMOVING THE BALL OF THE FEMUR

[76] Inventor: William B. Fischer, 707 N. Fairbanks Ct., Chicago, Ill. 60611

[21] Appl. No.: 250,943

[22] Filed: Sep. 29, 1988

Related U.S. Application Data

[60] Continuation-in-part of Ser. No. 58,913, Jun. 5, 1987, abandoned, which is a division of Ser. No. 820,549, Jan. 17, 1986, Pat. No. 4,714,478.

[51] Int. Cl.$^5$ .............................................. A61B 17/16
[52] U.S. Cl. ........................................ 606/84; 606/82
[58] Field of Search ...... 128/92 VY, 92 VV, 92 VW, 128/92 V, 305; 606/84, 82

[56] References Cited

U.S. PATENT DOCUMENTS

| | | | |
|---|---|---|---|
| 2,077,804 | 4/1937 | Morrison | 128/92 YW |
| 3,678,925 | 7/1972 | Fischer et al. | 128/92 YW |
| 3,702,611 | 10/1972 | Fishbein | 606/81 |
| 3,791,380 | 2/1974 | Dawidowski | 128/92 YW |
| 4,131,116 | 12/1978 | Hedrick | 128/92 VV |
| 4,157,715 | 6/1979 | Westerhoff | 128/92 ZY |
| 4,476,861 | 10/1984 | Dimakos et al. | 606/100 |
| 4,519,100 | 5/1985 | Wills et al. | 128/92 YW |
| 4,570,625 | 2/1986 | Harris et al. | 128/92 ZZ |
| 4,621,637 | 11/1986 | Fishbein | 128/92 V |
| 4,632,101 | 12/1986 | Freedland | 128/92 YY |
| 4,714,478 | 12/1987 | Fischer | 623/23 |
| 4,721,103 | 1/1988 | Freedland | 128/92 YT |

FOREIGN PATENT DOCUMENTS

| | | | |
|---|---|---|---|
| 856451 | 8/1981 | U.S.S.R. | 128/92 YW |
| 1055498 | 11/1983 | U.S.S.R. | 128/92 YW |

*Primary Examiner*—Robert A. Hafer
*Assistant Examiner*—Kevin G. Rooney
*Attorney, Agent, or Firm*—Willian Brinks Olds Hofer Gilson & Lione

[57] ABSTRACT

An endoprosthesis which comprises a flexible, collapsible, hollow device which can be filled after it is positioned within the bone structure. In the case of a prosthesis designed to replace the ball of the femur, the endoprosthesis has a ball portion, a neck portion attached to and communicating with the ball portion, a body portion attached to and communicating with the neck portion, and an access opening opposite the ball portion. A method for installing the endoprosthesis in the hip is also described, in which a portal is drilled through the lateral cortex of the femur at a location opposite the ball, the ball of the femur is removed, and the endoprosthesis is inserted through the portal. Finally, the invention provides a special tool that can be used for removing the ball of the femur through a portal in the lateral cortex without dislocating the hip. Generally, this tool comprises a rotatable shaft, a cutting blade received in an end portion of the shaft, and being hinged at its lower end, and means for extendig and retracting the blade.

16 Claims, 5 Drawing Sheets

TOOL FOR REMOVING THE BALL OF THE FEMUR

This application is a continuation-in-part of application Ser. No. 058,913, filed June 5, 1987 now abandoned which is a divisional application of application Ser. No. 820,549, filed Jan. 17, 1986, now U.S. Pat. No. 4,714,478.

BACKGROUND OF THE INVENTION

The present invention relates to a tool which enables the installation of a hip prosthesis by removal of the ball of the femur through a portal in the lateral cortex.

As a result of injuries, arthritis and other diseases, as well as degenerative processes that result from aging and/or the use of certain drugs, it often becomes necessary to surgically replace a ball-and-socket joint, i.e., the shoulder or hip, with a prosthesis. In the hip, the replacement of the head, or ball, of the hip with a metal endoprosthesis has become a relatively common surgical procedure. Often the acetabular cup is also replaced in a procedure commonly referred to as a "total hip replacement."

Not only is such a procedure often required in humans, but it is also sometimes required in animals such as dogs. However, owing to the expense of such a procedure, it is rarely performed on animals.

The installation of a conventional endoprosthesis requires that extensive muscle tissue be cut in order to expose the joint structure. In the case of a hip endoprosthesis, the hip itself must then be dislocated, the ball and neck removed, and marrow removed from the bone. The endoprosthesis has a long stem portion which is then installed in the cavity left by the removed marrow. The endoprosthesis is then cemented into place with a suitable cement such as methyl methacrylate.

A significant problem with the use of metal endoprostheses is their tendency to work loose and to become separated from the bone structure. While there are several causes for this, such loosening is unquestionably promoted by the difference in hardness between the endoprosthesis and the much softer surrounding bone structure. Breaking loose is also promoted by the inability of a metal endoprosthesis to conform to the interior of the femur. That is, the endoprosthesis must be shaped so that it can be slid into the bone, and this shape inevitably promotes breaking loose. Finally, the fact that the endoprosthesis is made of metal prevents the normal bending and compression of the femur in the area proximal to the stem.

Another problem with conventional endoprostheses is the high expense involved. Not only do surgical procedures tend to be lengthy and expensive, but the endoprostheses themselves are a significant expense. Such devices are expensive to manufacture, and a variety of sizes must be carried in inventory, since it is important to obtain as close a fit as possible for the individual patient.

Loosening is a particular problem in the case of a hip endoprosthesis, since that area of the body is subjected to frequent motion and is required to carry weight. When loosening of the endoprosthesis occurs, the correction of this problem usually requires a second major surgical procedure to remove the endoprosthesis and substitute one with a larger stem in order to fill the now enlarged interior of the femur. Such surgical procedures can be extremely traumatic, particularly in older patients, among whom the majority of hip replacements are performed.

Previous efforts at overcoming these problems have primarily been directed at attempts to improve the bonding between the endoprosthesis and the surrounding bone structure. For example, it is widely believed that a major source of loosening is that the curing of commonly used cements is an exothermic reaction which itself destroys some of the tissue on the interior of the femur. Such tissue destruction reduces the ability of the patient's tissue to grow and form a bond with the endoprosthesis. In an effort to correct this problem, "cementless" metal endoprostheses have been developed, which rely on a roughened surface into which the tissue can grow. Because time is required for such tissue growth, cementless endoprostheses greatly extend the healing time following surgery. Moreover, because it is made of metal, a cementless endoprosthesis will still tend to transmit shock to the bone, and, in many cases, will still tend to work loose.

Another problem with conventional metal endoprostheses is that the hard metal ball tends to destroy the relatively soft tissue of the joint socket. Thus, when an endoprosthesis is installed alone, it often becomes necessary to later replace the socket. As is well known in the art, the replacement of the socket itself can lead to an additional set of difficulties in that the replacement socket may tend to come loose.

Owing to the trauma involved in the surgery, and to the aging of the population, there is a growing number of people who need joint replacements, especially hip replacements, but cannot tolerate such surgery. Thus, there is a need for an endoprosthesis that can be installed with a method that involves significantly reduced trauma to the patient.

To this end, the endoprosthesis disclosed in U.S. Pat. No. 4,714,478 (Fischer) alleviates or even overcomes these problems by providing an endoprosthesis which is less prone to becoming detached after installation, which has a reduced tendency to cause wear to the hip socket, and which can be installed using a simpler and less traumatic procedure than was required by other devices.

Generally, the improved endoprosthesis disclosed by Fischer comprises a flexible, collapsible, hollow device which can be filled after it is positioned within the bone structure. In the case of a prosthesis designed to replace the ball of the femur, the endoprosthesis has a ball portion, a neck portion attached to and communicating with the ball portion, a body portion attached to and communicating with the neck portion, and an access opening opposite the ball portion. Because of this hollow, collapsible design, the body portion can be shaped to conform to the interior of the intermedullary space, including the trochanteric region and the stem region. This conformance allows the endoprosthesis to be retained in place by the bone structure itself, without any need for cement.

In addition, Fischer discloses procedures to install and replace the endoprosthesis that are less invasive, and thus less traumatic to the patient. In accordance with the method disclosed by Fischer, a flexible, collapsible, hollow hip endoprosthesis is installed by drilling a portal through the lateral cortex of the femur at a location opposite the ball, removing the ball of the femur, and inserting the endoprosthesis through the portal. The endoprosthesis is then positioned within the femur and is filled with a suitable material.

While the device and procedures taught by Fischer can be used in conjunction with conventional techniques to remove the ball of the femur, it is desirable to provide an arrangement which will remove the ball while preserving as much of the neck of the femur as possible.

Therefore in view of the above, it is a primary object of the present invention to provide a device which maybe used to remove the ball of the femur.

It is a further object of the present invention to provide a device which may be used to remove the ball of the femur while preserving a part of the neck of the femur.

SUMMARY OF THE INVENTION

The present invention provides a special tool that can be used for removing the ball of the femur through a portal in the lateral cortex without dislocating the hip. Generally, this tool comprises a rotatable shaft which includes a front end portion and a back end portion, a cutting blade received in the front end portion of the shaft, and being hinged at one end to the front end portion of the shaft. The tool further includes means for extending and retracting the blade. A forward direction is defined from the back end portion of the shaft to the front end portion of the shaft. The blade is hinged such that the nonhinged end of the blade projects in the forward direction when it is in the retracted position. The blade rotates in a backward direction. In this manner the tool may be inserted into the portal in the lateral cortex when the blade is in the retracted position.

DETAILED DESCRIPTION

Figure 1:
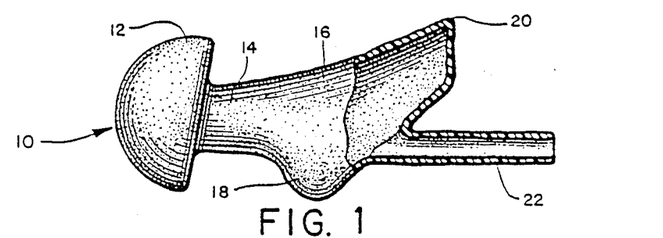
FIG. 1 is a side view of a hip endoprosthesis embodying the present invention, which is partially cut away to show the hollow interior thereof.
Figure 2:
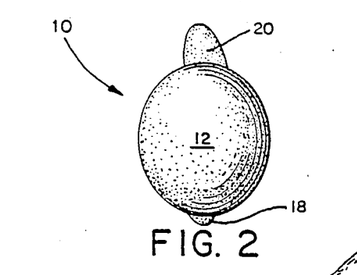
FIG. 2 is a top view thereof.
Figure 3:
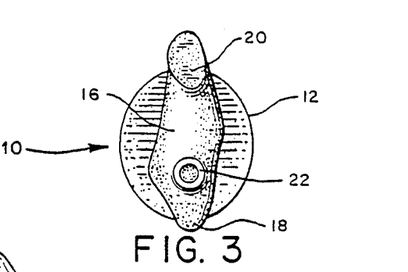
FIG. 3 is a bottom view thereof.

Referring to FIGS. 1-3, an endoprosthesis embodying the present invention is generally indicated by reference numeral 10. The endoprosthesis 10 is designed for use in the human hip. The endoprosthesis 10 is made of a flexible plastic material, and has a ball portion 12, a neck portion 14, and a body portion 16. The body portion 16 includes a trochanteric portion 18 and a stem portion 20. A hollow tube 22 projects from the bottom of the body portion 16 at a point opposite the ball portion 12. The tube 22 communicates with the interior of the endoprosthesis, as shown in FIG. 1.

Preferably, the endoprosthesis 10 will have a rough outer surface in order to help immobilize it within the femur, and to facilitate the engagement of the endoprosthesis with the surrounding tissue structure.

The endoprosthesis 10 can be installed using methods which are largely conventional, and which will be apparent to those skilled in the art. For example, a conventional "sunny side" incision can be made through the muscle, the hip dislocated, and the ball removed with a surgical saw. Because such a procedure involves considerable trauma to the patient, the technique described herein is preferred.

Figure 4:
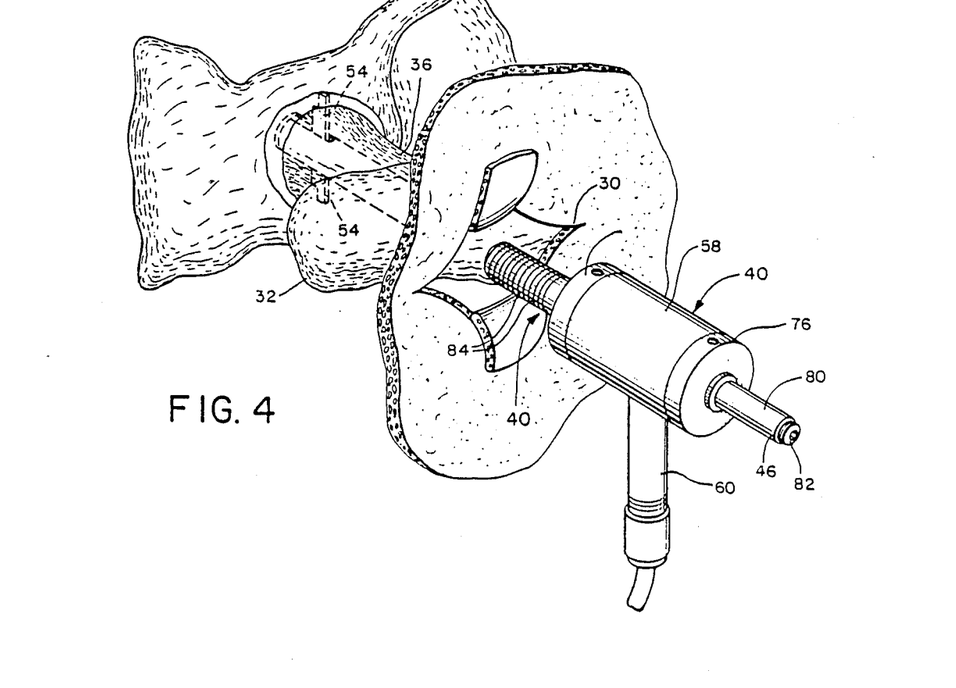
FIG. 4 is a fragmentary perspective view of a human hip, illustrating the manner in which the ball of the hip is removed.
Figure 5:
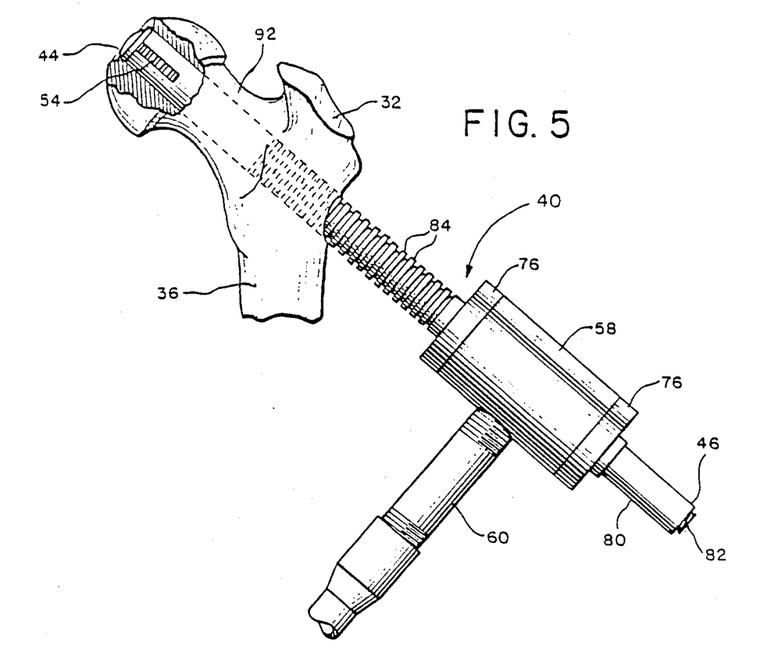
FIG. 5 is a perspective view of the upper portion of the femur, in which the view of the ball is partially cut away, showing the initial insertion of tool embodying the present invention.
Figure 6:
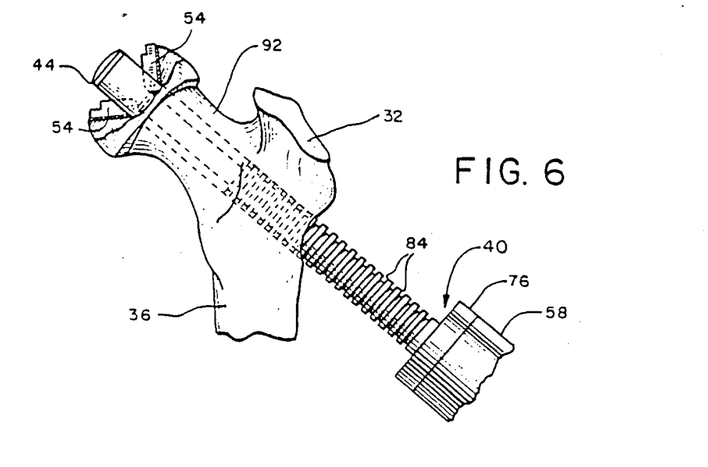
FIG. 6 is a perspective view similar to FIG. 5, showing the partial extension of the cutting blades of the tool during the cutting operation.

FIGS. 4-8 illustrate a preferred surgical procedure that may be used to install the endoprosthesis 10 with minimum trauma to the patient. Referring to FIGS. 4-6, in accordance with this method, the endoprosthesis 10 is installed by first making an incision 30 in the skin and tensor fascia adjacent the greater trochanter 32 and opposite the ball (not shown) of the femur 36. A pilot hole is then drilled with a guide pin (not shown) through the lateral cortex and the guide pin is passed through the center of the femoral neck. A larger portal is then drilled through the lateral cortex, centered on the pilot hole. Next, suitable x-ray equipment, such as a C-arm, is used to ensure proper centering of the guide pin in the head. A portal which is preferably about 0.5-1 inch in diameter is then drilled through the cortex. This portal should be as wide as the medullary space of the neck and should pass through the head of the ball. Up to this point, the procedure is well within the ability of those skilled in the art, and is similar to that used for compression head nailing for a fracture.

The next step in the installation procedure is the removal of the ball. As previously stated, this step may be accomplished by conventional techniques. However, while the neck is also conventionally removed, when using the endoprosthesis of the present invention, as much as possible of the neck should be preserved. In accordance with the preferred installation procedure, the novel tool of the present invention, generally indicated by reference numeral 40, is employed.

The detail of the tool 40 is best seen in FIGS. 9-15. The tool 40 includes a hollow, rotatable shaft 42 having a first end 44 and a second end 46. Since, as explained in more detail hereinafter, the first end 44 of the shaft 42 is inserted into the previously drilled hole, the direction defined from the second end 46 to the first end 44 of the shaft 42 is referred to hereinafter as the forward direction and the opposite direction is hereinafter referred to as the backward or reverse direction. An inner drive pin 48 moves longitudinally within the shaft 42. The drive pin 48 incorporates a piston 50 which fits closely within the shaft 42 in order to provide for hydraulic actuation of the pin 48 while permitting the passage of liquid for irrigation as hereinafter described.

Figure 9:
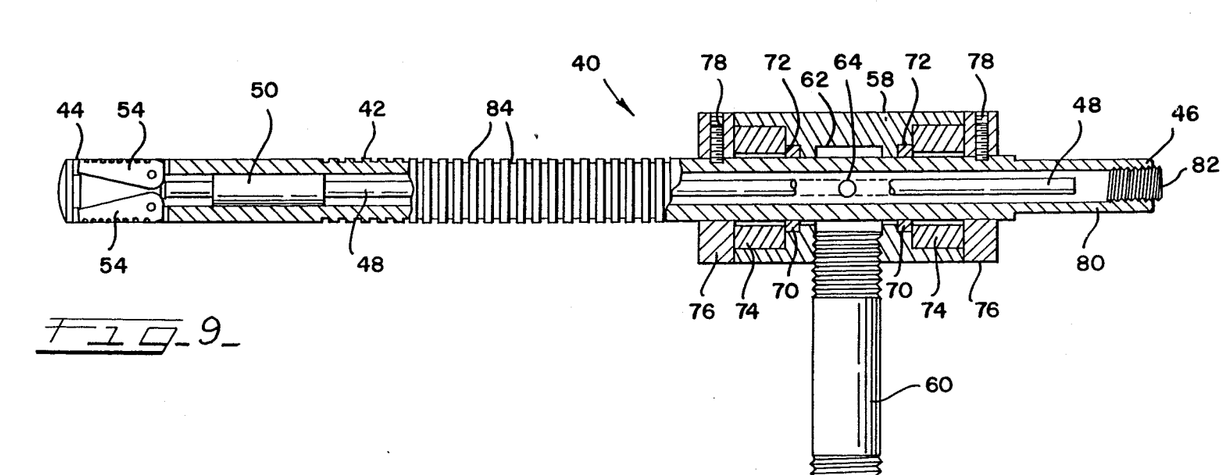
FIG. 9 is a side elevation view, partially in cross section, of a tool according to the invention.

The first end 44 of the shaft 42 has slots 52 within which serrated cutting blades 54 are hingedly mounted. Although the tool 40 would perform its desired function with only one such blade, it is preferred to employ two oppositely disposed blades 54 as shown.

To facilitate the insertion of the tool 40 in the previously drilled pilot hole in the lateral cortex and femoral neck, the blades 54 are preferably elongated and configured such that when in a retracted position the blades 54 lie substantially within the outer radius of the shaft 42. The blades 54 are pivotally mounted to the shaft 42 such that the blades 54 expand in a backward direction.

Figure 11:
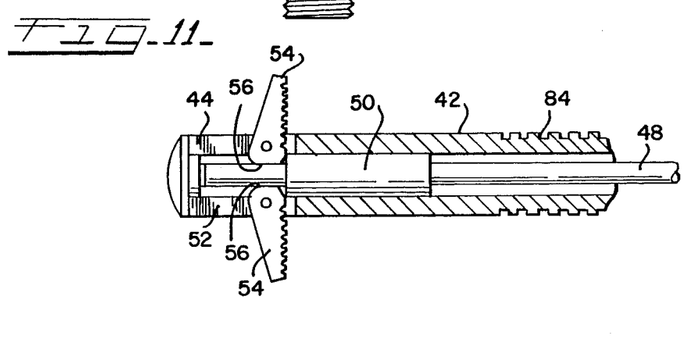
FIG. 11 is a fragmentary cross-sectional view similar to FIG. 10, showing the cutting blades fully extended.

Each blade 54 has a cammed surface 56 which contacts the end of the drive pin 48 when the pin 48 is in the retracted position as shown in FIG. 9. It is thus seen that the piston 50 and drive pin 48 form means for extending and retracting the blades. As shown in FIG. 11, the cammed surface 56 is preferably designed to permit the end of the drive pin 48 to move past the blades 54, and to lock them in their fully extended position.

Referring to FIG. 9, the shaft 42 is free to rotate within a housing 58 having a liquid inlet conduit 60 on the side thereof. The liquid inlet conduit 60 communicates with a chamber 62 within the housing 58. The chamber 62 in turn communicates with the interior of the shaft 42 via an aperture 64. The housing 58 has a pair of O-rings 70 mounted in recesses 72 adjacent each side of the chamber 62 to prevent liquid from escaping from the chamber 62. The O-rings 70 are held in place by retainer rings 74, which, in turn, are held in place by end caps 76. The end caps 76 rotate with the shaft 42, and are held in place by set screws 78. The second end 46 of the shaft 42 has a narrowed portion 80, and is closed by a plug 82.

In the preferred embodiment shown, the shaft 42 has circumferential grooves 84 cut into it at regular intervals. These grooves 84 aid in measuring the penetration distance when using x-ray equipment.

Referring now specifically to FIGS. 12-15, a preferred embodiment of the blade 54 comprises an elongated wedged shaped body 102 with a plurality of teeth 101 disposed on the longitudinal inclined face 106 of the wedged shaped body 102.

Figure 12:
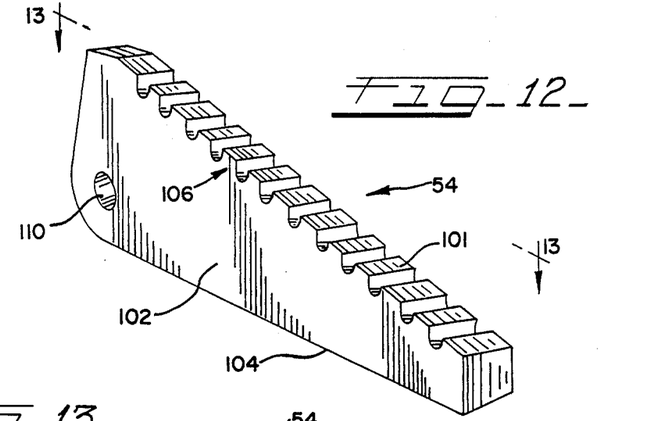
FIG. 12 is a perspective view of a preferred embodiment of a cutting blade comprising a part of the tool of the present invention.
Figure 13:
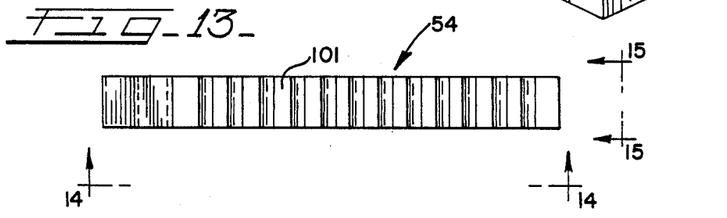
FIG. 13 is a top view through lines 13—13 of the cutting blade of in FIG. 12.

As best illustrated in FIGS. 12 and 13 the teeth 101 of the blade 54 are preferably graded across the width of the blade 54. The width of the blade is defined here as the narrow dimension of the blade 54.

In an exemplary embodiment the angle $\theta_1$ between the inclined face 106 and the bottom face 104 of the blade 54 is 16° and the angle $\theta_3$ of the grade of the teeth 101 is 5°. The back surface 108 of the blade is also preferably inclined at a predetermined angle $\theta_2$ relative to a plane normal to the bottom face 104 of the blade 54. In an exemplary embodiment $\theta_2$ is also 16°.

The teeth 101 of the blade 54 may incorporate any suitable serration arrangement. In a preferred embodiment the blades 54 are made of a stainless-steel material and the teeth 101 are 0.040 inches apart; 0.020 inches deep; and 0.040 inches along the direction of the inclined face 106 and the width of the blade is 0.100 inches.

Since the interior of the ball is softer than the outer surface of the ball, in another preferred embodiment the dimension of the teeth 101 along the direction of the inclined face 106 is successively smaller for each tooth from the back of the blade 54 to the front of the blade 54. That is, the length of each tooth 101 from the back of the blade 54 to the front of the blade 54 is slightly smaller than the length of the previous tooth. In addition to being graded, the teeth 101 may also be arranged on an angle relative to the width of the blade 54.

Figure 14:
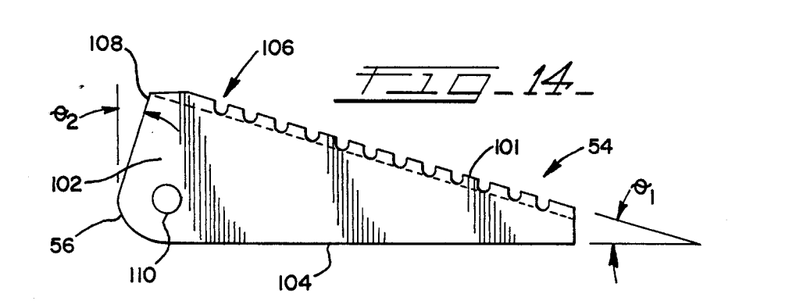
FIG. 14 is a side elevational view through lines 14—14 of the cutting blade of FIG. 13.
Figure 15:
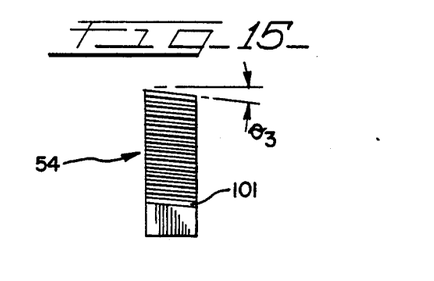
FIG. 15 is a front view through lines 15—15 of the cutting blade of FIG. 13.

As illustrated in FIGS. 12 and 14 the blade 54 includes a bore 110 at the bottom of one end of the blade 54. The bore 110 is used in cooperation with a pivot pin in the shaft 40 to pivotally attach the blade 54 to the shaft 40. Since, as illustrated in FIG. 9, when the blade 54 is an a retracted position, the narrower portion of the wedge shaped body 102 of the blade 54 projects in the forward direction, the narrower portion of the wedge is referred to here as the front of the blade and the wider portion of the wedge shaped body 102 (which includes the bore 110) is referred to here as the back portion of the blade 54.

Referring again to FIGS. 4-6, to remove the ball of the femur with the tool 40, the liquid inlet conduit 10 is connected to a source of liquid under pressure. A sterile and biologically safe liquid, such as sterile Ringer's solution or saline solution, preferably with an antibiotic additive, should be employed.

The narrowed portion 80 of the tool 40 is connected to drive means, preferably driven through a flexible drive shaft (not shown). As best shown in FIG. 5, the first end 44 of the shaft 42 is then inserted into the previously drilled hole until the first end 44 passes through the ball and contacts the hip socket (not shown). As will be recognized by those skilled in the art the outer diameter of the shaft 40 may be any suitable diameter which will allow insertion of the shaft 40 into the previously drilled pilot hole. A preferred outer diameter is 0.625 inches.

Fluid under pressure is delivered through the inlet conduit 60, exerting pressure against the piston 50 and urging the drive pin 48 toward the first end 44 of the shaft 42. Since the expansion of the blades 54 will depend on the fluid pressure delivered through the inlet conduit 60, the operating range of pressures is preferably sufficiently high to allow precise expansion of the blades to be easily and accurately implemented.

Figure 10:
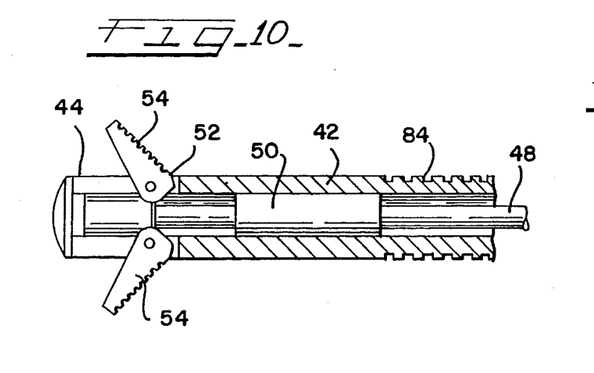
FIG. 10 is a fragmentary cross-sectional view showing the end portion of the tool shown in FIG. 9 with the cutting blades partially extended.

In a preferred embodiment the size of the piston is such that the operating range of pressures is between 28 and 30 psi. The shaft 42 is then rotated at a controlled rate of speed, preferably in the range of 0 to about 300 rpm. The slower rates are used at the beginning and end of the ball-removal procedure, while higher rates of speed can be used for removal of the major portion of the ball. As shown in FIGS. 6 and 10, the liquid pressure will cause the end of the pin 48 to push against the cammed surfaces 56 of the blades 54, urging them outwardly, thereby grinding the ball into a fine powder. As illustrated best in FIG. 6, the blades 54 extend in a backward direction such that the ball is removed from the top center portion of the head to the portion of the head connected to the neck. It will be recognized by those skilled in the art that if the portion of the head which is attached to the neck were removed first, the remaining portion would rotate freely thereby preventing the rotating blades 54 from grinding the remaining portion.

In a preferred embodiment a predetermined distance is provided between the top of the first end 44 of the shaft 40 and the top of the blades 54. Since the top of the first end 44 engages the acetabular surface, this predetermined distance preserves the acetabular surface during the deheading process.

As more of the ball is removed on each successive rotation, the blades will move farther outwardly until they reach the position shown in FIGS. 4 and 11. In that position, the cammed surfaces 56 have moved over center, permitting the pin 48 to move past them and to lock the blades 54 in their fully extended position, as previously described. Rotation of the shaft 42 is continued, while the shaft is slowly withdrawn, cutting away the remainder of the ball. The completion of this procedure is shown in FIG. 4. It will be recognized by those skilled in the art that the ground particles of the ball need to be periodically removed by known irrigation and aspiration techniques.

To further protect the acetabular surface the tool 40 may include a spring (not shown) disposed at the tip of the first end 44. With this arrangement, the physician must exert a force sufficient to compress the spring against the acetabular surface when the tool 40 is first inserted. As the removal process is initiated and the blades 54 expand, the force of the blades against the ball with retain the spring in the compressed position. The spring will urge the tool 40 in a backward direction such that a space is maintained between the free ends of the blades 54 and the acetabular surface.

The disclosed embodiments of the tool 40 provides an arrangement which will efficiently remove the ball of the femur through a portal drilled through the lateral cortex and femoral head without dislocating the hip. Since, when in a retracted position, the blades 54 are preferably disposed within the radius of the shaft 40, the tool is easily inserted into the pilot hole. The blades 54 then expand outwardly in a backward direction to remove the ball by grinding it into a fine powder. This arrangement allows the tool of the present invention to be inserted through a portal in the neck without the need to remove the neck completely.

Since the blades 54 are preferably serrated, as the shift 40 rotates and the blades 54 expand, the bone is ground without chipping the bone. This is desirable since chipping would generate larger pieces of removed bone which could not be easily removed by irrigating and aspirating techniques. The grade of the teeth 101 across the width of the blades 54 also facilitates the grinding procedure by preventing the serrated face 106 from engaging the bone at a normal angle.

After the ball has been entirely removed, the liquid pressure is stopped, and suction is applied, causing the pin 48 to move out of engagement with the blades 54. As the shaft 42 is withdrawn, the blades 54 will retract into the slots 52. The fragments left behind are then removed from the hip socket area by irrigation and aspiration.

Figure 7:
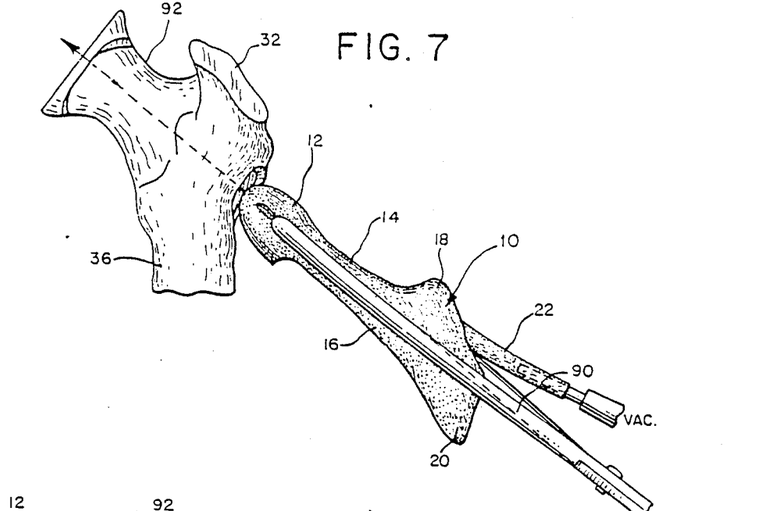
FIG. 7 is a perspective view similar to FIG. 5, showing the use of forceps to insert the collapsed endoprosthesis into the femur.

Referring now to FIG. 7, the next step is the insertion of the endoprosthesis 10. A suitable amount of marrow is removed from the interior of the femur 36 to allow room for the endoprosthesis 10. In the preferred installation method, the air is withdrawn from the endoprosthesis 10, and with the hollow tube 22 is closed off. The endoprosthesis 10 will therefore be collapsed, as shown in FIG. 7. The endoprosthesis 10 is then inserted through the portal in the femur using a forceps 90. As shown in FIG. 7, the endoprosthesis 10 is preferably folded to make it easier to insert it into the lateral portal. The endoprosthesis 10 should be passed through the femur 36 until the ball portion 12 seats on the femoral neck 92.

The next step is to fill the endoprosthesis 10. In accordance with the present invention, the endoprosthesis 10 can be filled with any suitable material, which can include liquids or particulate solids. Because of the possibility of eventual rupture of the wall of the endoprosthesis, any such material must, of course, be sterile and biologically safe.

Figure 8:
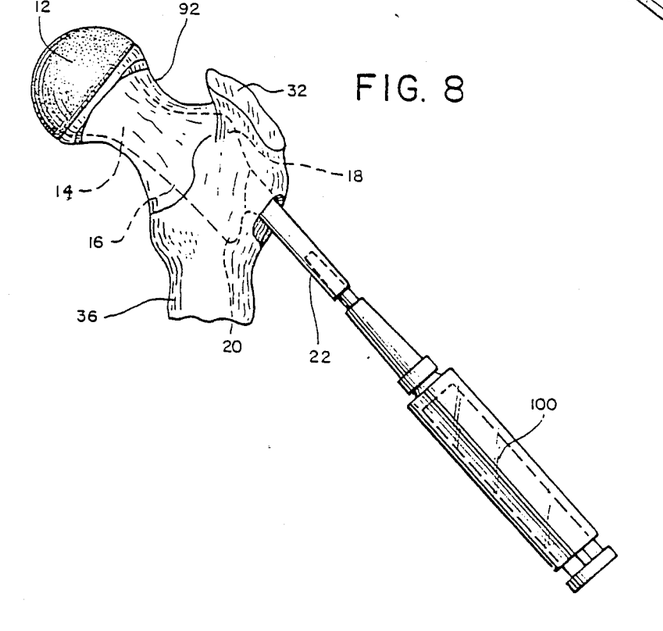
FIG. 8 is a perspective view similar to FIG. 5, showing the femur showing the inflation and filling of the endoprosthesis.

In accordance with the preferred embodiment, the endoprosthesis 10 is filled with a suitable plastic and curing agent. As shown in FIG. 8, this is preferably accomplished by mixing the two liquid components of the elastomer and placing them in a syringe 100 just prior to use. If the endoprosthesis 10 has already been evacuated, then the mixed elastomer components will simultaneously fill and inflate it. Once the elastomer is in place, the hollow tube 22 is cut off, and the incision is closed.

While the particular materials used to manufacture and fill the endoprosthesis 10 form no part of this invention, it is obvious that these materials must have certain characteristics. The plastic material used to form the endoprosthesis 10 must be resilient so that it will spring back to its original shape, and must be sufficiently flexible to permit the endoprosthesis 10 to be positioned within the femur as described above. The material must also have sufficient strength that it will not erode upon constant contact with the hip socket, and must also be compatible with body tissue. Finally, the material must be one that can be readily molded into the desired shape.

The presently preferred material for forming the endoprosthesis 10 is a silicone elastomer. Such materials are available as two separate components (elastomer and catalyst) from Dow Chemical Corporation, Midland, Michigan, under the trademark Silastic. A particularly preferred material is marketed by Dow as Silastic Q7-4840 A/B Medical Grade Liquid Silicone Rubber. These and other suitable elastomers are described and claimed in U.S. Pat. Nos. 3,445,420 and 4,162,243. These materials are also suitable for filling the endoprosthesis following insertion as previously described.

The endoprosthesis itself is preferably formed by molding, with the interior cavity being defined by a wax, which is subsequently removed by melting. Preferably, the wax has a melting point in the range of 200°–210° F. It is also important that the mold be evacuated prior to filling in order to minimize the formation of air bubbles. Such techniques are well within the skill of those familiar with the molding art.

Although the preferred embodiment of the endoprosthesis 10 described above is designed to replace the ball of the human hip, modifications of the device to render it suitable as a shoulder ball replacement will be obvious to those skilled in the art. Similarly, it will be obvious that an endoprosthesis embodying the present invention can be used in connection with the repair of ball-and-socket joints in animals such as dogs.

Obviously many modifications and variations of the invention as set forth herein will occur to those skilled in the art, and it is intended that the following claims will cover all such modifications and variations as fall within the true spirit and scope of the invention.

I claim:

1. A tool for removing the ball of the femur through an aperture passing through the lateral cortex and femoral neck comprising:
   a. a rotatable shaft having a front end portion and a back end portion, wherein a forward direction is defined from said back end portion to said front end portion;

b. a cutting blade hingedly mounted at one end to said front end portion of said shaft, said blade having a retracted position and an open position, the other end of said blade projecting in said forward direction when said blade is in said retracted position such that said other end of said blade is adapted to rotate in a backward direction;

c. means for extending and retracting said blade; and d. drive means attached to said shaft for rotating said shaft and said blade about the longitudinal axis of said shaft, such that said ball of the femur is ground by said blade upon rotation of said shaft and said blade.

2. The tool as defined in claim 1 wherein said blade is adapted to pass through said aperture when in said retracted position.

3. The tool as defined in claim 1 wherein two oppositely disposed blades are hingedly mounted in said front end portion of said shaft.

4. The tool as defined in claim 3 wherein said blades are adapted to pass through said aperture when in said retracted position.

5. The tool as defined in claim 1 wherein said shaft includes a slot in said front end portion and wherein said blade is received in said slot.

6. The tool as defined in claim 5 wherein said blade comprises a wedge shaped body including a pair of longitudinally extending side walls and a plurality of teeth disposed on an inclined face, said inclined face disposed between said pair of longitudinally extending side walls of said wedge shaped body.

7. The tool as defined in claim 6 wherein one of said longitudinally extending walls has a height greater than the other of said longitudinally extending walls such that said teeth are inclined between said longitudinally extending walls of said blade.

8. The tool as defined in claim 3 wherein said means for extending and retracting the blades comprise a piston axially movable within said shaft, said piston engaging said blades; and means for delivering liquid to said shaft opposite said blades to exert fluid pressure on said piston, said piston causing said blades to extend when said piston is moved toward said blades and to permit said blades to retract when said piston is moved away from said blades.

9. The tool as defined in claim 8 further comprising means for locking said blades in their fully extended position.

10. A tool for removing the ball of the femur through an aperture passing through an aperture passing through the lateral cortex and femoral neck comprising:

a. a rotatable shaft having a front end portion and a back end portion, wherein a forward direction is defined from said back end portion to said front end portion;

b. a cutting blade hingedly mounted at one end to said front end portion of said shaft said blade having a retracted position and an open position the other end of said blade projecting in said forward direction when said blade is in said retracted position such that said other end of said blade is adapted to rotate in a backward direction, said blade adapted to pass through said aperture when in said retracted position;

c. means for extending and retracting said blade; and d. drive means attached to said shaft for rotating said shaft and said blade about the longitudinal axis of said shaft, such that said ball of the femur is ground by said blade upon rotation of said shaft and said blade.

11. The tool as defined in claim 10 wherein two oppositely disposed blades are hingedly mounted in said front end portion of said shaft.

12. The tool as defined in claim 10 wherein said blade comprises a serrated blade.

13. The tool as defined in claim 12 wherein said blade comprises a wedge shaped body including a pair of longitudinally extending side walls and a plurality of teeth disposed on an inclined face, said inclined face disposed between said pair of longitudinally extending side walls of said wedge shaped body.

14. The tool as defined in claim 13 wherein one of said longitudinally extending walls has a height greater than the other of said longitudinally extending walls such that said teeth are inclined between said longitudinally extending walls of said blade.

15. The tool as defined in claim 11 wherein said means for extending and retracting the blades comprise a piston axially movable within said shaft, said piston engaging said blades; and means for delivering liquid to said shaft opposite said blades to exert fluid pressure on said piston, said piston causing said blades to extend when said piston is moved toward said blades and to permit said blades to retract when said piston is moved away from said blades.

16. The tool as defined in claim 15 further comprising means for locking said blades in their fully extended position.

* * * * *